United States Patent
Patton

(10) Patent No.: US 11,937,954 B2
(45) Date of Patent: Mar. 26, 2024

(54) SYSTEMS AND METHODS FOR COMBINED FEMTO-PHACO SURGERY

(71) Applicant: Lensar, Inc.

(72) Inventor: Douglas Patton, Irvine, CA (US)

(73) Assignee: Lensar, Inc., Orlando, FL (US)

( * ) Notice: Subject to any disclaimer, the term of this patent is extended or adjusted under 35 U.S.C. 154(b) by 0 days.

(21) Appl. No.: 15/974,405

(22) Filed: May 8, 2018

(65) Prior Publication Data

US 2018/0250090 A1 Sep. 6, 2018

Related U.S. Application Data

(63) Continuation-in-part of application No. 15/791,385, filed on Oct. 23, 2017, now abandoned.

(Continued)

(51) Int. Cl.
*A61B 34/00* (2016.01)
*A61B 50/24* (2016.01)
(Continued)

(52) U.S. Cl.
CPC .............. *A61B 50/24* (2016.02); *A61B 34/25* (2016.02); *A61B 50/33* (2016.02); *A61B 90/25* (2016.02); *A61F 9/00736* (2013.01); *A61F 9/00781* (2013.01); *A61F 9/00825* (2013.01); *A61F 9/0084* (2013.01); *A61B 2034/2048* (2016.02); *A61B 2034/254* (2016.02); *A61B 50/13* (2016.02); *A61B 2217/005* (2013.01); *A61B 2217/007* (2013.01);
(Continued)

(58) Field of Classification Search
CPC ......... A61B 50/24; A61B 34/25; A61B 50/33; A61B 90/25; A61B 2560/0437; A61B 50/13; A61B 50/15; A61B 2050/155; A61B 2034/2048; A61B 2034/2046; A61F 9/00736

See application file for complete search history.

(56) References Cited

U.S. PATENT DOCUMENTS

| 4,729,373 A | 3/1988 | Peyman |
| 4,825,865 A | 5/1989 | Zelman |

(Continued)

FOREIGN PATENT DOCUMENTS

| EP | 2057973 | 5/2009 |
| JP | 2015 02964 | 2/2015 |

(Continued)

OTHER PUBLICATIONS

International Search Report dated May 13, 2019, for PCT application No. PCT/US2018/054254, filed Oct. 3, 2018. 3 pages.

(Continued)

*Primary Examiner* — Allen Porter
*Assistant Examiner* — Adreanne A. Arnold
(74) *Attorney, Agent, or Firm* — Glen P. Belvis; Belvis Law, LLC.

(57) ABSTRACT

Systems and methods are described for a combined Femto and Phaco surgical system built into a single housing. The system advantageously permits each of the Femto device and Phaco surgical tray to be rotated out of the way or into the position without requiring movement of a patient. Thus, a user can switch between Femto and Phaco surgical procedures without movement of the patient.

19 Claims, 16 Drawing Sheets

Related U.S. Application Data

(60) Provisional application No. 62/411,441, filed on Oct. 21, 2016.

(51) Int. Cl.

| | | |
|---|---|---|
| *A61B 50/33* | (2016.01) | |
| *A61B 90/25* | (2016.01) | |
| *A61F 9/007* | (2006.01) | |
| *A61F 9/008* | (2006.01) | |
| A61B 34/20 | (2016.01) | |
| A61B 50/13 | (2016.01) | |

(52) U.S. Cl.
CPC .............. *A61B 2560/0437* (2013.01); *A61F 2009/0087* (2013.01); *A61F 2009/00872* (2013.01)

(56) References Cited

U.S. PATENT DOCUMENTS

| | | | |
|---|---|---|---|
| 4,946,452 A | 8/1990 | Py | |
| 4,963,142 A | 10/1990 | Loertscher | |
| 5,057,098 A | 10/1991 | Zelman | |
| 5,098,426 A | 3/1992 | Sklar | |
| 5,139,504 A | 8/1992 | Zelman | |
| 5,423,801 A | 6/1995 | Marshall | |
| 5,439,462 A | 8/1995 | Bille et al. | |
| 5,548,352 A | 8/1996 | Dewey | |
| 5,591,160 A | 1/1997 | Reynard | |
| 5,651,783 A | 7/1997 | Reynard | |
| 5,695,461 A | 12/1997 | Schaible | |
| 5,722,970 A | 3/1998 | Colvard et al. | |
| 5,741,244 A | 4/1998 | Klaas | |
| 6,045,527 A | 4/2000 | Appelbaum | |
| 6,055,458 A | 4/2000 | Cochran et al. | |
| 6,391,020 B1 | 5/2002 | Kurtz | |
| 6,544,254 B1 | 4/2003 | Bath | |
| 6,733,491 B2 | 5/2004 | Kadziauskas | |
| 6,736,360 B1* | 5/2004 | Buczek | A61B 50/10 248/278.1 |
| 6,962,583 B2 | 11/2005 | Kadziauskas et al. | |
| 7,182,759 B2 | 2/2007 | Kadziauskas | |
| 8,986,290 B2 | 3/2015 | Patton | |
| 9,050,171 B2 | 6/2015 | Foster | |
| 9,095,415 B2 | 8/2015 | Blumenkranz et al. | |
| 9,107,732 B2 | 8/2015 | Blumenkranz et al. | |
| 9,259,354 B2 | 2/2016 | Horvath | |
| 9,492,318 B2 | 11/2016 | Rockley et al. | |
| 9,545,335 B2 | 1/2017 | Boukhny et al. | |
| 10,709,610 B2 | 7/2020 | Morley et al. | |
| 10,722,388 B2 | 7/2020 | Kim et al. | |
| 2001/0035702 A1* | 11/2001 | Murphy | A61B 50/10 312/285 |
| 2003/0050629 A1 | 3/2003 | Kadziauskas | |
| 2003/0073984 A1 | 4/2003 | Maeda | |
| 2004/0034340 A1 | 2/2004 | Biscup | |
| 2007/0027470 A1 | 2/2007 | Dodick | |
| 2007/0237620 A1 | 10/2007 | Muhlhoff | |
| 2008/0004608 A1 | 1/2008 | Dacquay | |
| 2008/0013048 A1* | 1/2008 | Gaida | A61F 9/008 351/205 |
| 2008/0071254 A1 | 3/2008 | Lummis | |
| 2009/0137991 A1 | 5/2009 | Kurtz | |
| 2009/0137993 A1 | 5/2009 | Kurtz | |
| 2010/0243590 A1* | 9/2010 | Ross | A61B 50/10 211/131.2 |
| 2011/0022035 A1 | 1/2011 | Porter | |
| 2011/0288470 A1 | 11/2011 | Boukhny | |
| 2012/0022510 A1* | 1/2012 | Welches | A61B 18/22 606/14 |
| 2012/0316544 A1* | 12/2012 | Horvath | A61F 9/00825 606/4 |
| 2013/0023864 A1 | 1/2013 | Blumenkranz | |
| 2013/0090636 A1* | 4/2013 | Patton | A61F 9/00825 606/6 |
| 2014/0046308 A1* | 2/2014 | Bischoff | A61F 9/008 606/4 |
| 2014/0052113 A1 | 2/2014 | Kuehnert | |
| 2014/0104576 A1 | 4/2014 | Bor et al. | |
| 2014/0107634 A1 | 4/2014 | Vogler | |
| 2014/0276677 A1* | 9/2014 | Brownell | A61F 9/00836 606/5 |
| 2014/0343541 A1 | 11/2014 | Scott et al. | |
| 2014/0364870 A1 | 12/2014 | Alvarez et al. | |
| 2015/0190281 A1 | 7/2015 | Patton | |
| 2016/0045367 A1 | 2/2016 | Horvath | |
| 2016/0089269 A1 | 3/2016 | Horvath | |
| 2016/0331584 A1* | 11/2016 | Ren | G06F 3/0482 |
| 2017/0000645 A1 | 1/2017 | Summers et al. | |
| 2017/0000647 A1 | 1/2017 | Schuele et al. | |
| 2017/0056245 A1 | 3/2017 | Rockley et al. | |
| 2017/0119249 A1 | 5/2017 | Gunn | |
| 2017/0119578 A1 | 5/2017 | Rockley et al. | |
| 2017/0128259 A1 | 5/2017 | Goh et al. | |
| 2017/0246036 A1* | 8/2017 | Kraemer | A61F 9/00736 |
| 2017/0290703 A1 | 10/2017 | Teuma et al. | |
| 2017/0340483 A1 | 11/2017 | Rill et al. | |
| 2018/0028355 A1 | 2/2018 | Raksi | |
| 2018/0085256 A1 | 3/2018 | Gray et al. | |
| 2018/0085257 A1 | 3/2018 | Horvath et al. | |
| 2018/0161051 A1 | 6/2018 | Humayun | |
| 2018/0168547 A1* | 6/2018 | Kim | A61B 8/4405 |
| 2018/0168859 A1 | 6/2018 | Bischoff | |
| 2018/0185043 A1 | 7/2018 | Humayun | |
| 2018/0206717 A1 | 7/2018 | Ramesh Kumar et al. | |
| 2018/0250090 A1 | 9/2018 | Patton | |
| 2019/0083308 A1 | 3/2019 | Rathjen | |
| 2019/0096933 A1 | 3/2019 | Kido et al. | |
| 2019/0365567 A1 | 12/2019 | Balkenbush et al. | |
| 2021/0259880 A1 | 8/2021 | Newton et al. | |
| 2021/0259881 A1 | 8/2021 | Gray et al. | |
| 2021/0298955 A1 | 9/2021 | McWhirter et al. | |
| 2021/0378864 A1 | 12/2021 | Teuma et al. | |

FOREIGN PATENT DOCUMENTS

| | | |
|---|---|---|
| WO | WO1992017138 | 10/1992 |
| WO | WO1997022304 | 6/1997 |
| WO | WO1998012973 | 4/1998 |
| WO | WO 1999065405 | 12/1999 |
| WO | WO2006074469 | 7/2006 |
| WO | WO2009039315 | 3/2009 |
| WO | WO2009061758 | 5/2009 |
| WO | WO2012047492 | 4/2012 |
| WO | WO 2013057098 | 4/2013 |
| WO | WO2013126653 | 8/2013 |
| WO | WO2014201165 | 12/2014 |

OTHER PUBLICATIONS

Nagy, Zoltan Z.; et al. "Femtosecond laser cataract surgery;" Nagy and McAlinden Eye and Vision. Jun. 20, 2015. 8 pages.
Jul. 7, 2021, WIPO, PCT/US21/12008—Opinion and search report.
Apr. 6, 2021, WIPO, PCT/US21/12009—Opinion and search report.
May 25, 2021, WIPO, PCT/US21/12010—Opinion and search report.
Jun. 25, 2021, WIPO, PCT/US12011—Opinion and search report.
May 13, 2019, WIPO, PCT/US18/54254—Opinion and search report.

* cited by examiner

Phaco Mode

SYSTEMS AND METHODS FOR COMBINED FEMTO-PHACO SURGERY

This application is a continuation-in-part application of U.S. patent application having Ser. No. 15/791,385 filed on Oct. 23, 2017, which itself claims priority to U.S. provisional application having Ser. No. 62/411,441 filed on Oct. 21, 2016. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is Femto-Phaco Surgery.

BACKGROUND

The following description includes information that may be useful in understanding the present invention. It is not an admission that any of the information provided herein is prior art or relevant to the presently claimed invention, or that any publication specifically or implicitly referenced is prior art.

Typically, a patient undergoing cataract surgery that involves a Femto laser and Phacoemulsification has to be wheeled from one operating room where the Femto laser is located then to finish the surgery to another room where the Phaco machine is located. This is obviously not good for the patient. In addition, Applicant is unaware of any system that shares procedural patient data information between the Femto machine and Phaco machine. Because of this deficiency, a surgeon is not permitted to build on previous surgery data or combine procedures between the two machines. In addition, there exists no way to easily transition between the two machines during surgery for detail patient modifications.

Although great work has been done to address these problems, such as described in U.S. Pat. No. 8,986,290 to Patton, more work needs to be done to improve the patient outcome and eliminate the above problems.

Thus, there is still a need for an all-in-one machine that can eliminate the need to move patients during procedures and that allows for the sharing of patient data information for both procedures.

SUMMARY OF THE INVENTION

The inventive subject matter provides apparatus, systems and methods for a combined Femto-Phaco surgical apparatus—e.g., a machine or system that can utilizes both a Femto laser and Phacoemulsification without requiring movement of the patient and that allows for patient information obtained before or during a first procedure to be used in the subsequent procedure. Contemplated systems advantageously employ swivel technology that allows a practitioner to easily articulate radially the Femto and Phaco arms into position during surgery without requiring patient movement. The two arms are also not required to articulate over the main housing.

This combination Femto-Phaco surgical apparatus as described herein is the future of ophthalmology, and has application and benefits for every surgery. The core of the system is the swivel technology that allows a surgeon or other professional to easily articulate radially the Femto and Phaco arms into position during surgery, without requiring movement of the patient or the device itself. The arms are not required articulate over the main housing.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
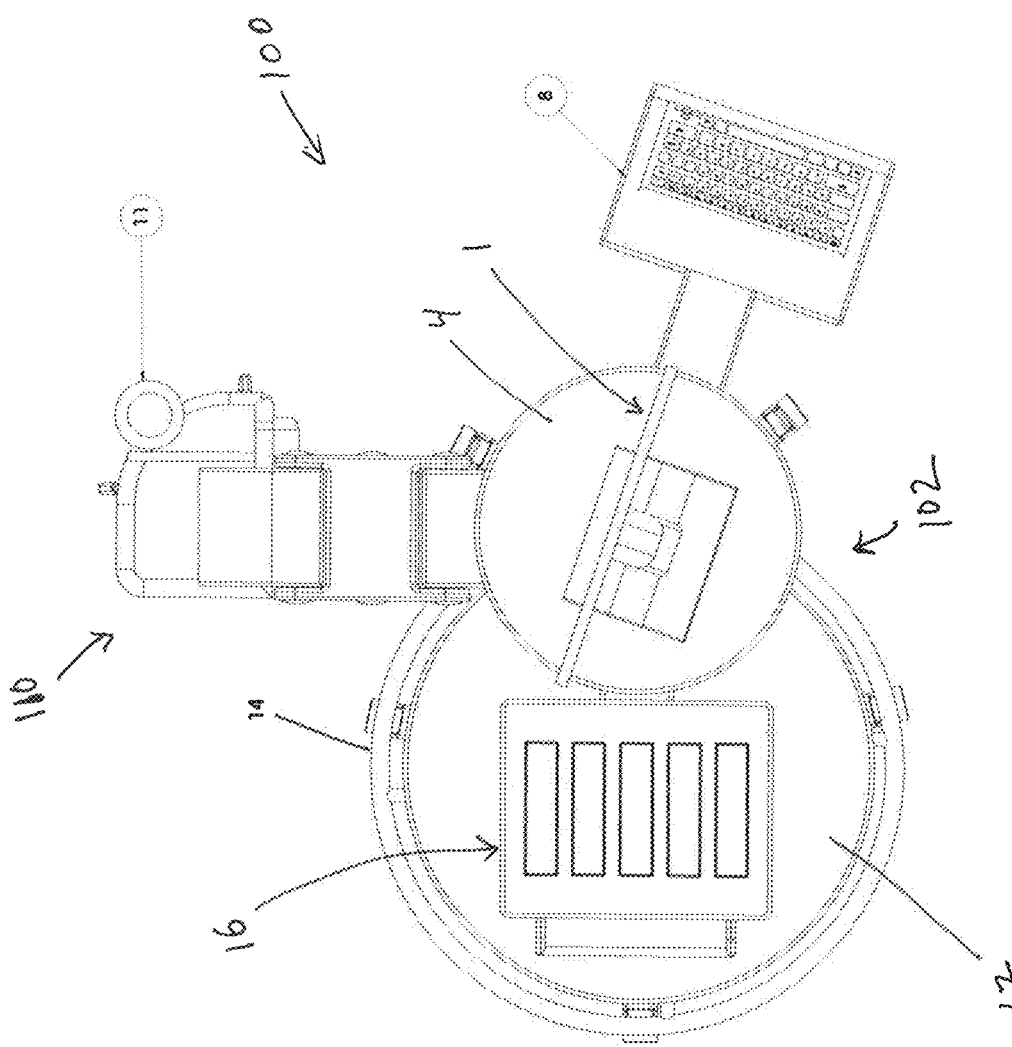
FIGS. 1-4 illustrate various views of one embodiment of a combination surgical device in cataract Phaco mode.
Figure 2:
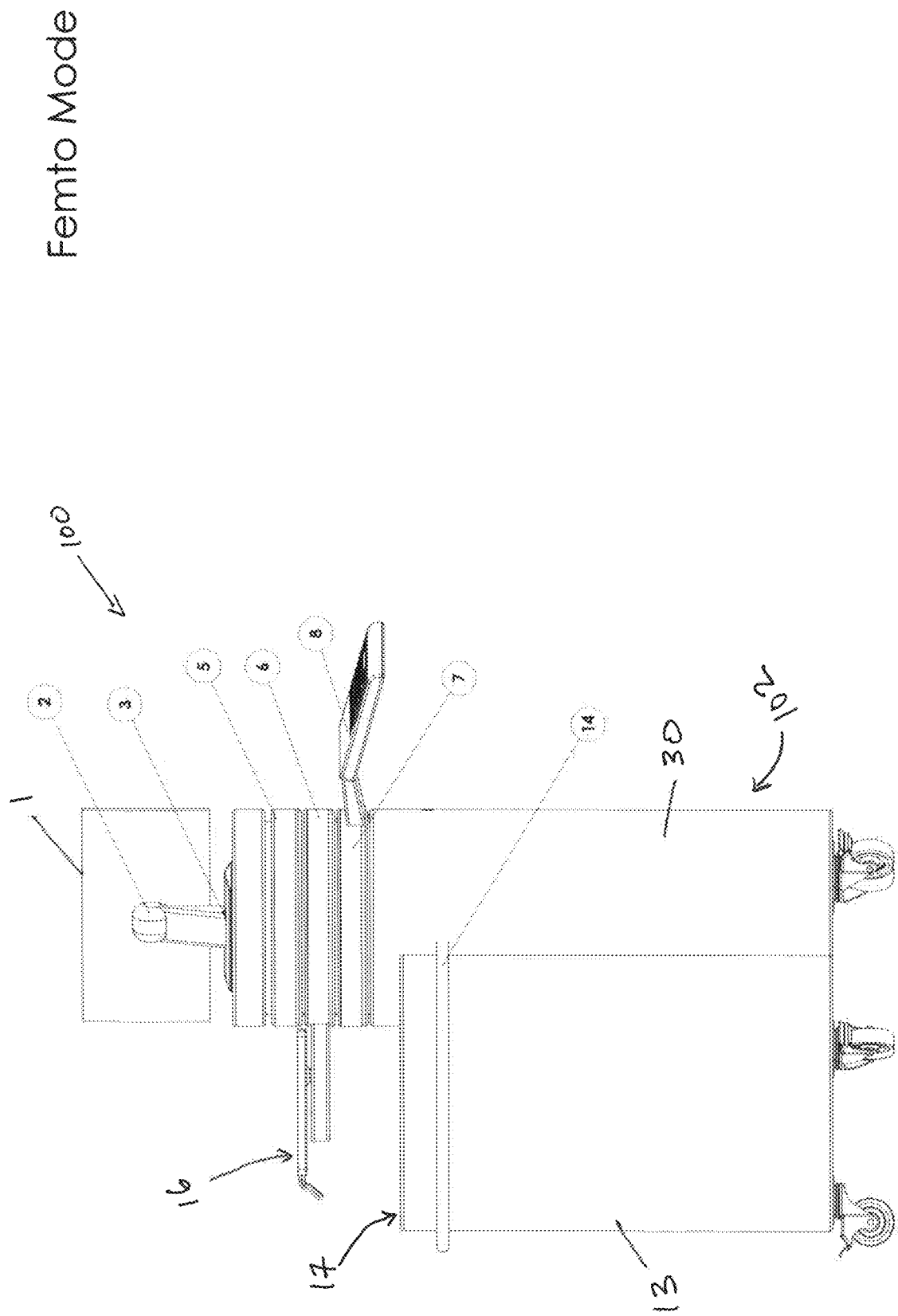

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

FIGS. 1-8 illustrate various views of one embodiment of a combination surgical device 100. FIGS. 1-4 illustrates the device 100 in a cataract Phaco configuration, while FIGS. 5-8 illustrate the device 100 in a Femto configuration.

As shown in the Figures, device 100 comprises a housing 102 for the Femto and Phaco components, which can include a plurality of wheels 15 at the bottom to permit easy movement of the device 100 within a room or between rooms, for example. The device 100 can have a built-in power supply and/or be connected with an external power supply such as a line voltage. Likewise, the device 100 can have various inputs and outputs, as needed, which could include an Ethernet port, a HMDI or other video out port, as well as a wireless transceiver for sending and receiving data.

Housing 102 preferably comprises a first portion 13 and a second portion 30 coupled to one another with the first portion 13 having a larger perimeter and/or diameter of the second portion 30. The first portion has a housing top 17 above which various components of the device 100 can be stored when not in use, to help prevent damage to the components and ensure they are not in the way. It is contemplated that the first portion can include one or more handles 14 to permit easy grasp of the device 100 such as for movement.

Various components can be disposed within the first and second portions 13, 30 as discussed below and shown in FIG. 16.

The second portion 30 preferably includes a plurality of swivels 5-7, each of which can be attached to a different component required for the Femto and/or Phaco procedures. Each of the plurality of swivels 5-7 is disposed about a single axis that runs vertically through at least a portion of the second portion 30, and each can be articulated or rotated about the axis to thereby move an attached component with respect to the housing 102.

Figure 5:
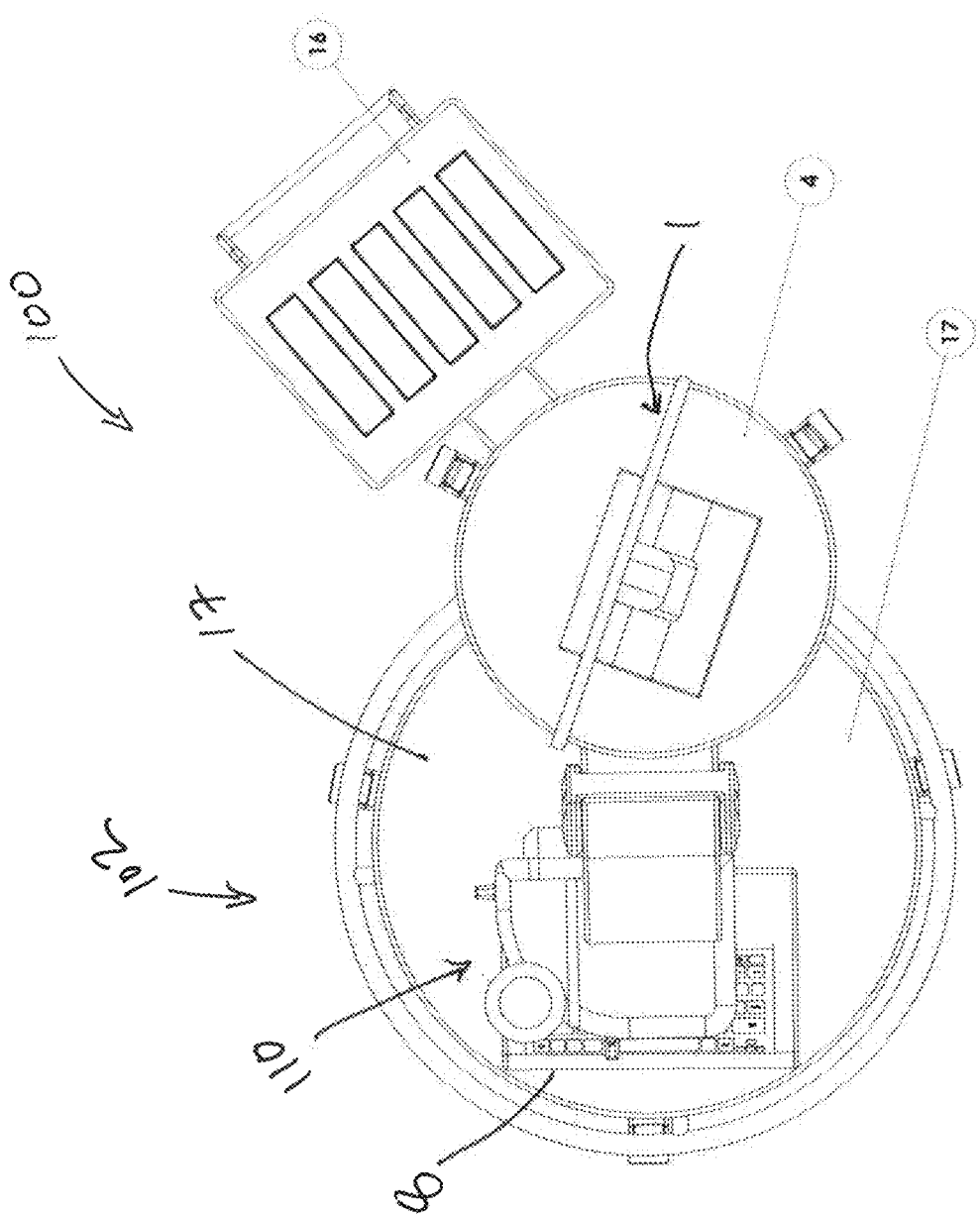
FIGS. 5-8 illustrate various views of the combination surgical device of FIG. 1 in Femto mode.
Figure 6:
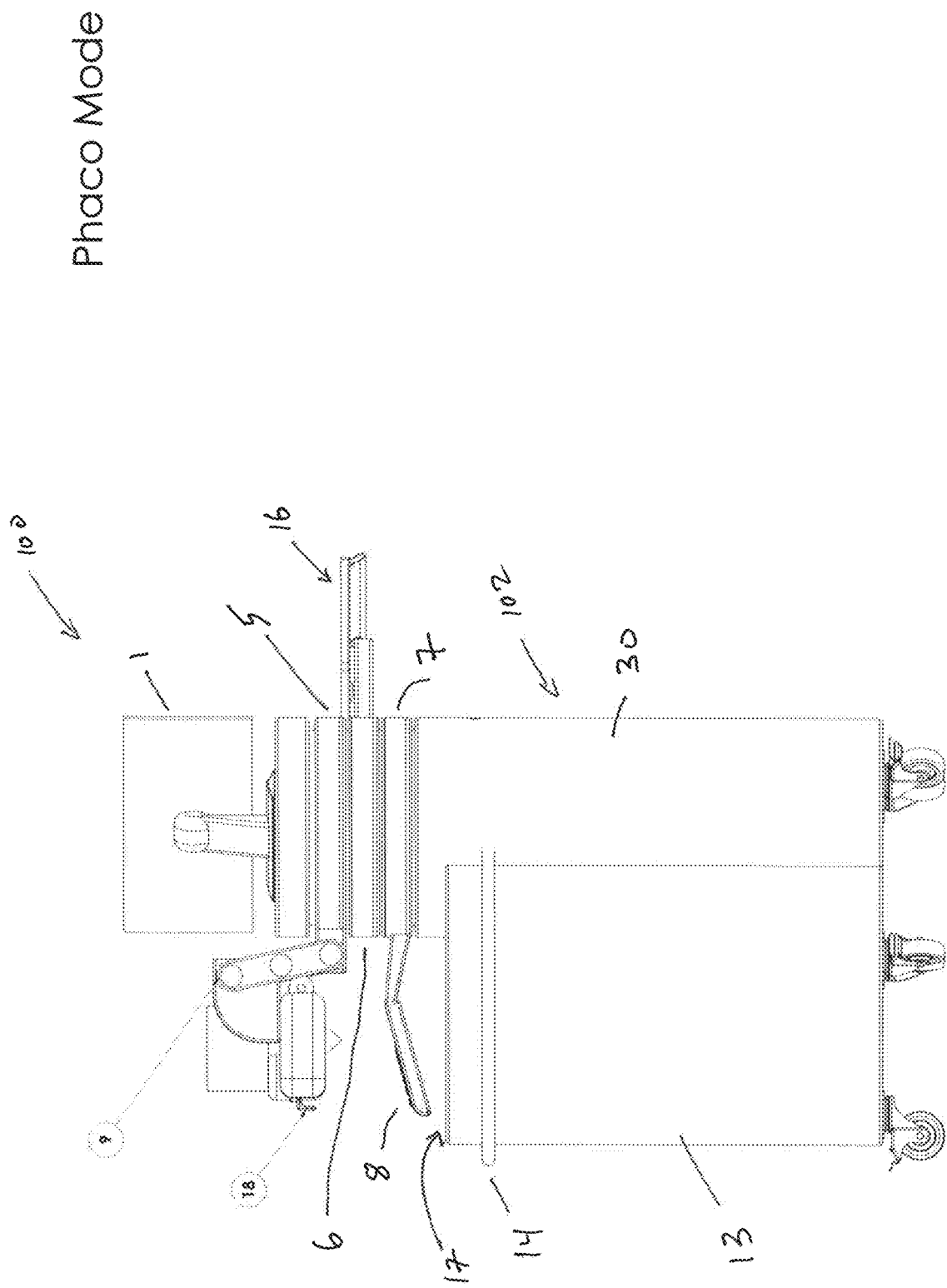

Device 100 further includes a power column Femto keyboard swivel 7 disposed on the second portion 30 or power column, to which a keyboard 8 can be coupled for use during the Femto procedure. This keyboard swivel 7 advantageously permits the keyboard 8 to be moved into position when needed and then swiveled or pivoted out of the way when not necessary. For example, as shown in FIG. 5, when not in use, the swivels 5, 7 permit the keyboard 8 and Femto device 110 to be rotated to a position above the housing top 17 such that they will not be disturbed or impede the work required for the Phaco procedure.

Figure 3:
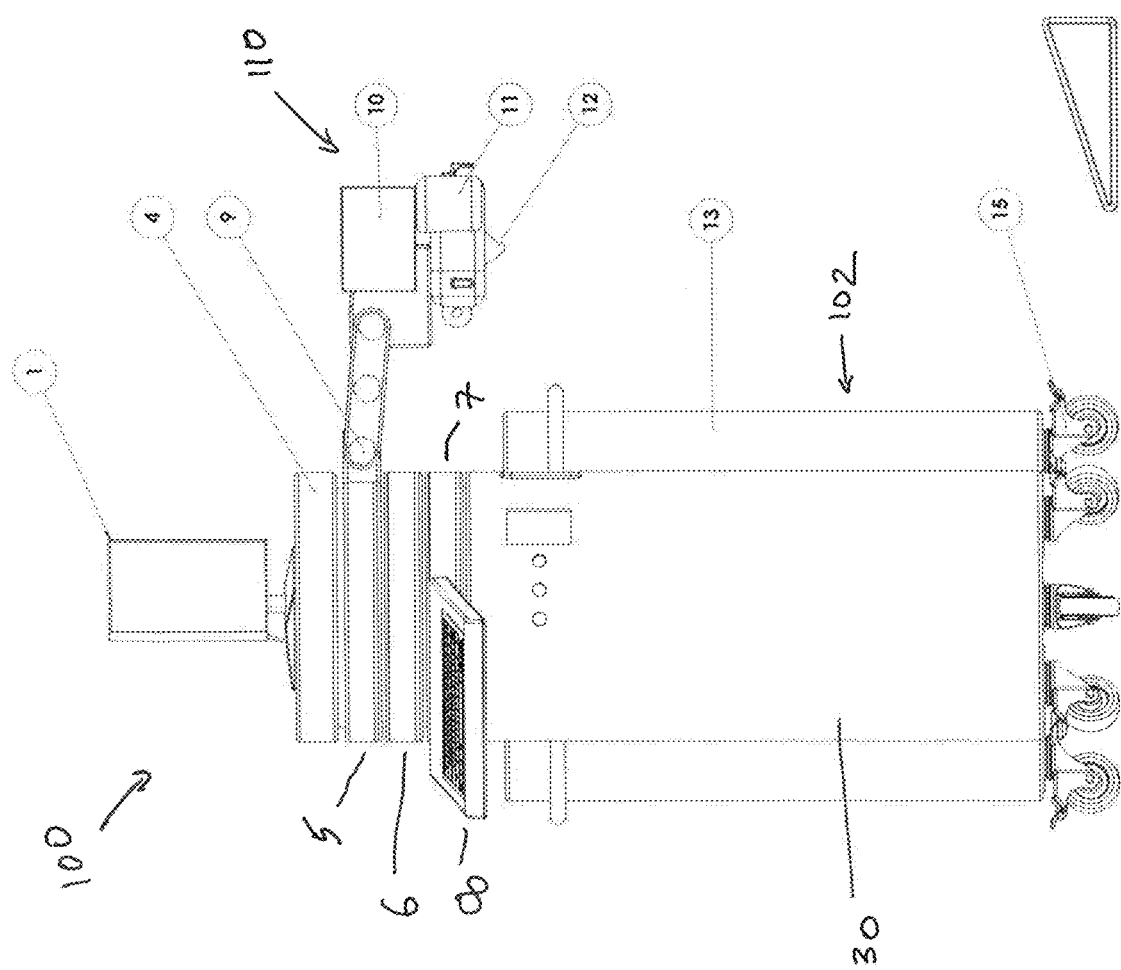
Figure 4:
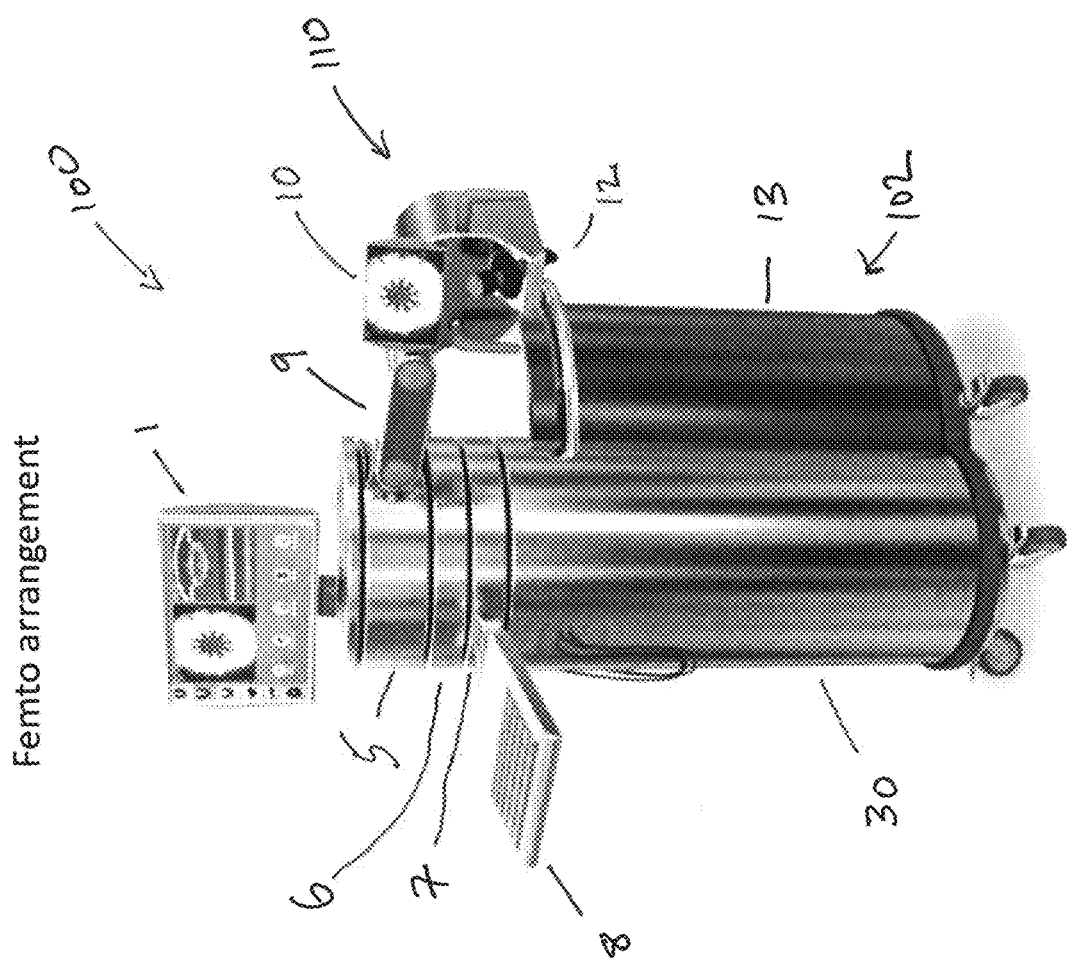
Figure 12:
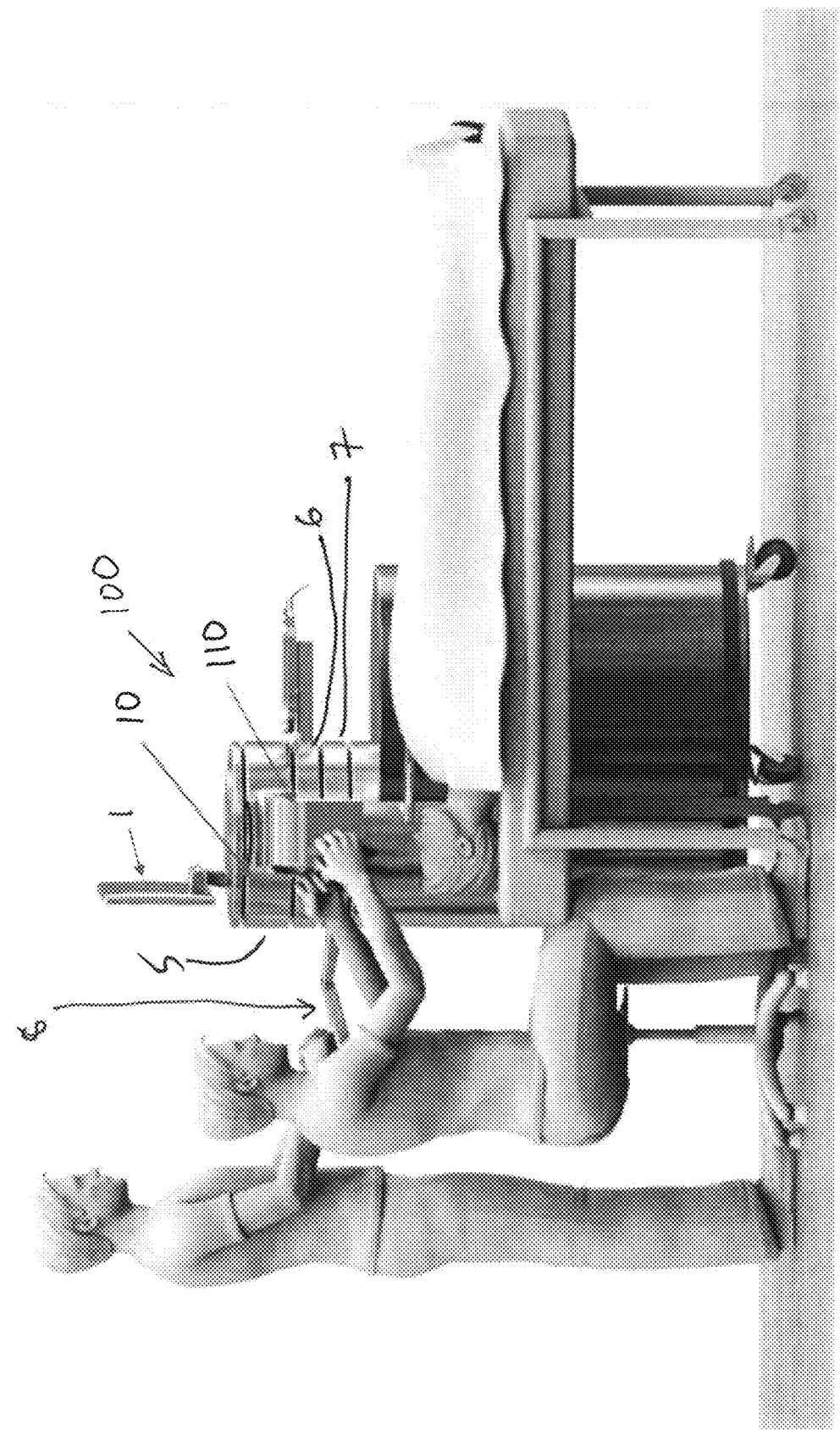
FIGS. 12-13 illustrate various views of the combination surgical device of FIG. 1 in Femto mode.
Figure 13:
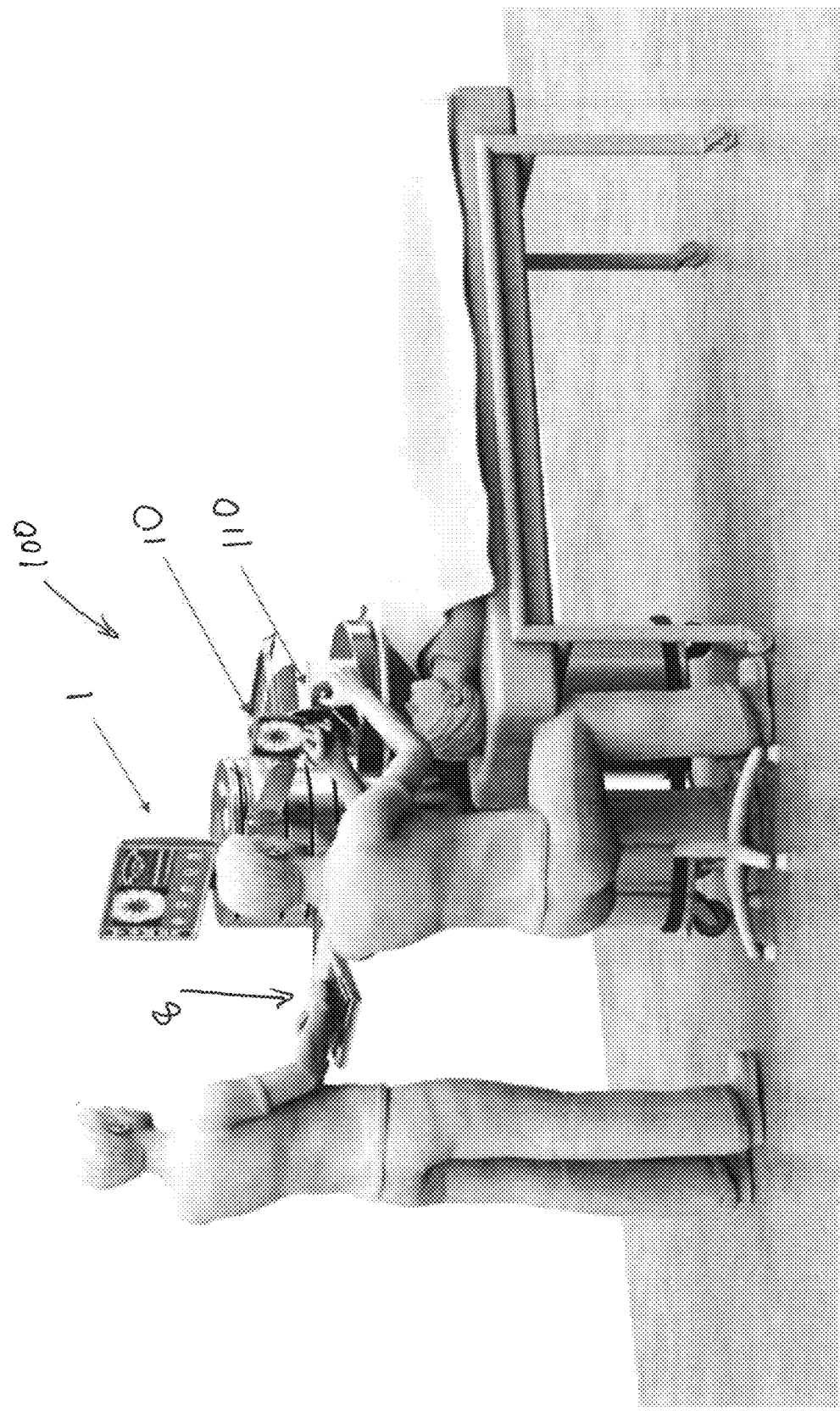

A power column Femto laser head swivel 5 can be disposed above the keyboard swivel 7. A Femto device 110 can be coupled to the swivel 5, as shown in FIG. 3. The Femto device 110 preferably includes an articulated optical arm 9 coupled to the swivel 5. A surgeon display 10 for the Femto device, along with a Femto laser head 11 and Femto disposable cornea centration device 12 is coupled to the optical arm 9. The articulated arm 9 permits the device 110 to be placed in a specific position relative to a patient, such as shown in FIGS. 12-13, and permits movement of the Femto device 110 in three dimensions relative to the device 100.

In some contemplated embodiments, the Femto device 110 can include one or more accelerometers that record and send a precise position of the laser head 11, such that its precise location and position can be recorded. The accelerometer will record a precise position in x, y, and z axes. This information is critical, as it permits the laser head 11 to be returned to exactly the same position, such as if the Femto device is moved to permit a Phaco procedure to occur before returning to the use of the Femto laser head 11. The movement of the Femto device 110 and/or swivel 5 can be controlled via a user interface, such as that shown in FIG. 9.

The precise position of the swivel 5 or arm 9 could also be recorded using any commercially suitable sensors known in the art.

With the precise location and position information of the Femto device saved, it is contemplated that this information could be used to automatically return the Femto device 110 to the precise position it was in before the Femto device 110 was moved for example. Thus, it is contemplated that the swivel 5 could be coupled with a motor such that the swivel can automatically be rotated about its axis to a precise position with respect to housing 30. Likewise, the laser head 11 and/or other components of the Femto device 110 can be automatically moved/repositioned as necessary to return the components to a preset position. This can be accomplished via any commercially suitable mechanism.

In this manner, should an ophthalmologist or other professional wish to switch from the Femto procedure to a Phaco procedure and then back to the Femto procedure, the Femto device 110 could be automatically returned to its precise position, such as shown in FIG. 12-13, after the user completes the Phaco procedure. This is all without requiring movement of the patient. By automatically returning the Femto device 110 to its prior position, this saves significant time and helps ensure the overall success and safety of the procedure.

A monitor swivel 4 can be coupled to the top portion of the device 100, which supports one or more monitors 1 and permits movement of the monitor 1 with respect to the housing 13 as needed. To permit ease of viewing the monitor for practitioners of different heights, for example, the monitor 1 can be disposed on a monitor arm 2 and tilt structure 3, which permits the variation of the angle of the face of the monitor 1 with respect to the monitor swivel 4. The monitor 1 preferably presents a user interface such as described below to observe and control the procedures. In some embodiments, monitor 1 permits input via a touch-screen, although it is also contemplated that inputs to device 100 can be received via keyboard 8, voice command, or other inputs.

Device 100 can further include a Phaco surgical tray swivel 6 to which a surgical tray 16 for use with the Phacoemulsification procedure can be attached. In this manner, the Phaco surgical tray 16 can be moved out of the way when not in use and preferably moved above housing 13, and specifically above the housing top 17, such as shown in FIG. 1.

The Phaco surgical tray 16 could be preferably with the tray swivel 6 via an articulated arm, which would permit vertical and/or horizontal movement of the Phaco surgical tray 16. The Phaco surgical tray 16 preferably comprises a brake release adjustment 18 to lock the surgical tray 16 in place, such as during the procedure. This helps ensure that accidental bumping or weight on the tray 16 will not move it. Tray 16 could hold or store one or more tools used in the Phaco procedure, including for example Phaco, infrared (IR) and vitrectomy (VIT) hand pieces.

Figure 7:
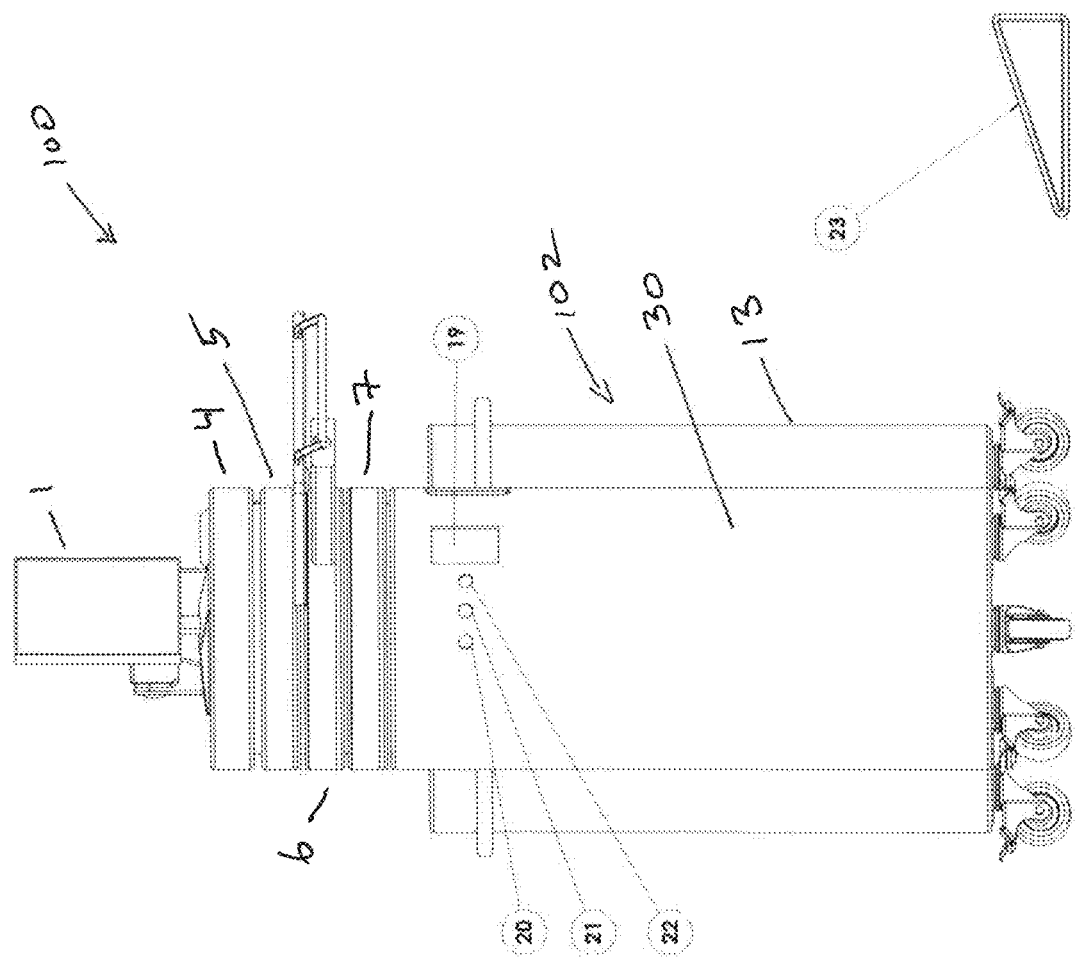
Figure 8:
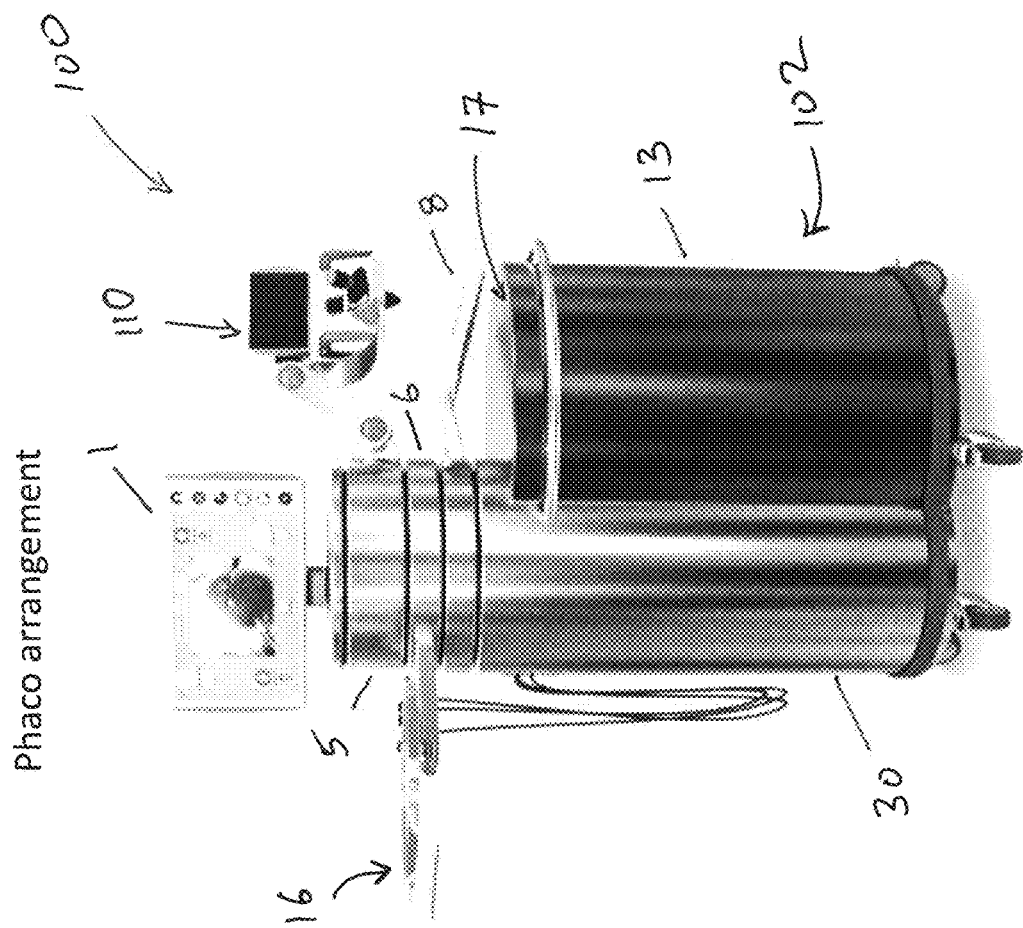

As shown in FIG. 7, the second portion 30 of the housing 102 can comprise a Phaco fluidics module and cassette 19, as well as various connectors 20-22 required for the procedures. Such connectors can include, for example, a Phaco connector 20, an aspiration connector 21, and an irrigation connector 22. The hand pieces discussed above can be coupled with these connectors, such as shown in FIG. 15.

Device 100 further comprises a foot pedal 23 for control of the procedures. Preferably the foot pedal 23 is wirelessly connected to the device 100 and therefore can be moved as needed to be in the most convenient position for whoever is operating device 100. While the foot pedal 23 could communicate with device 100 via a wired connection, a wireless connection such as WWI or Bluetooth™ is preferred because it eliminates the wire as a potential tripping hazard.

Figure 14:
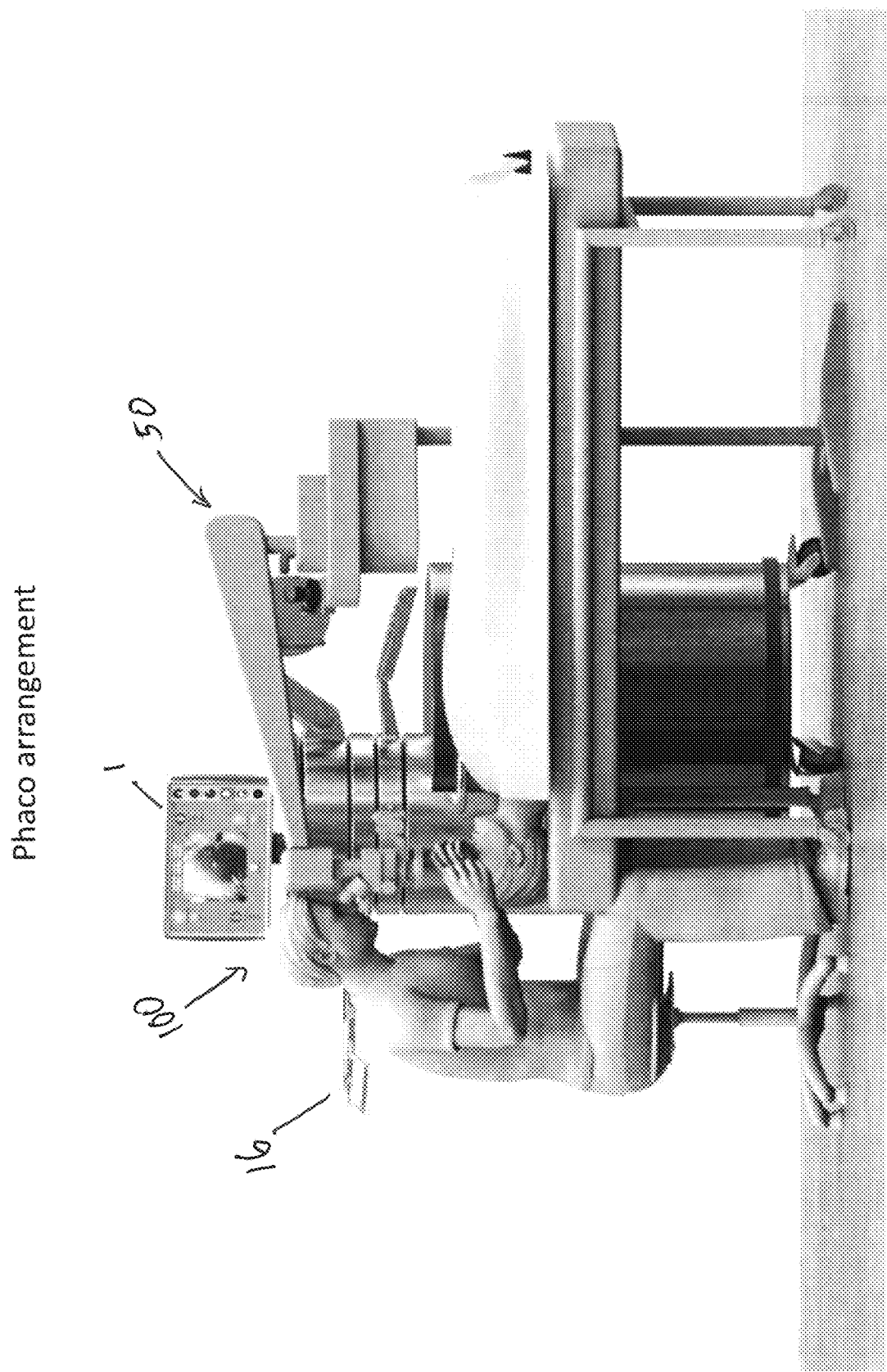
FIGS. 14-15 illustrate various views of the combination surgical device of FIG. 1 in Femto mode.
Figure 15:
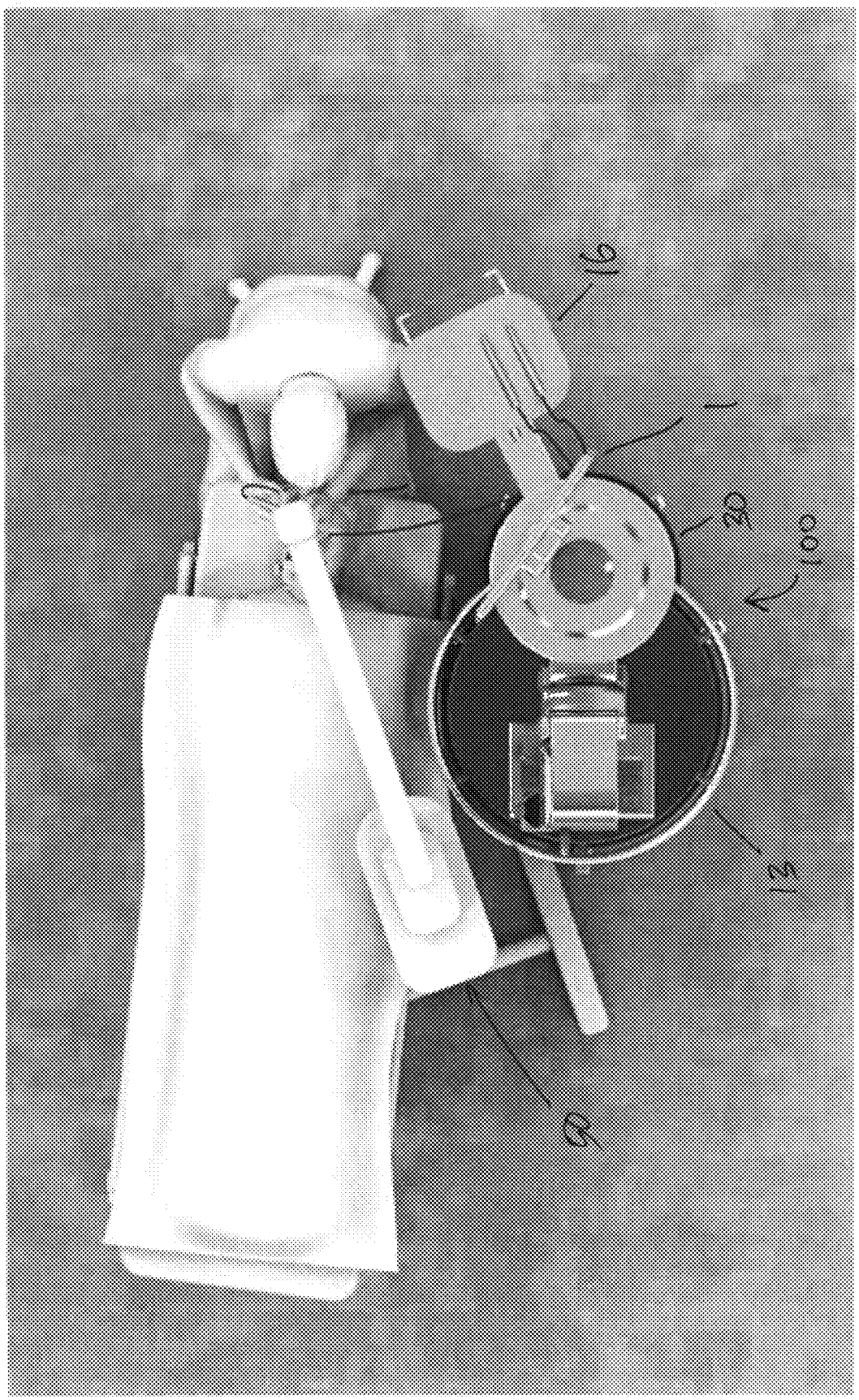

FIGS. 14-15 illustrate device 100 in a Phaco arrangement as would be used with a patient. Although a microscope 50 is shown adjacent to the device 100, it is contemplated that the microscope 50 could be integrated into the device 100 and could be coupled to the power column 30 via a distinct swivel for example.

Figure 9:
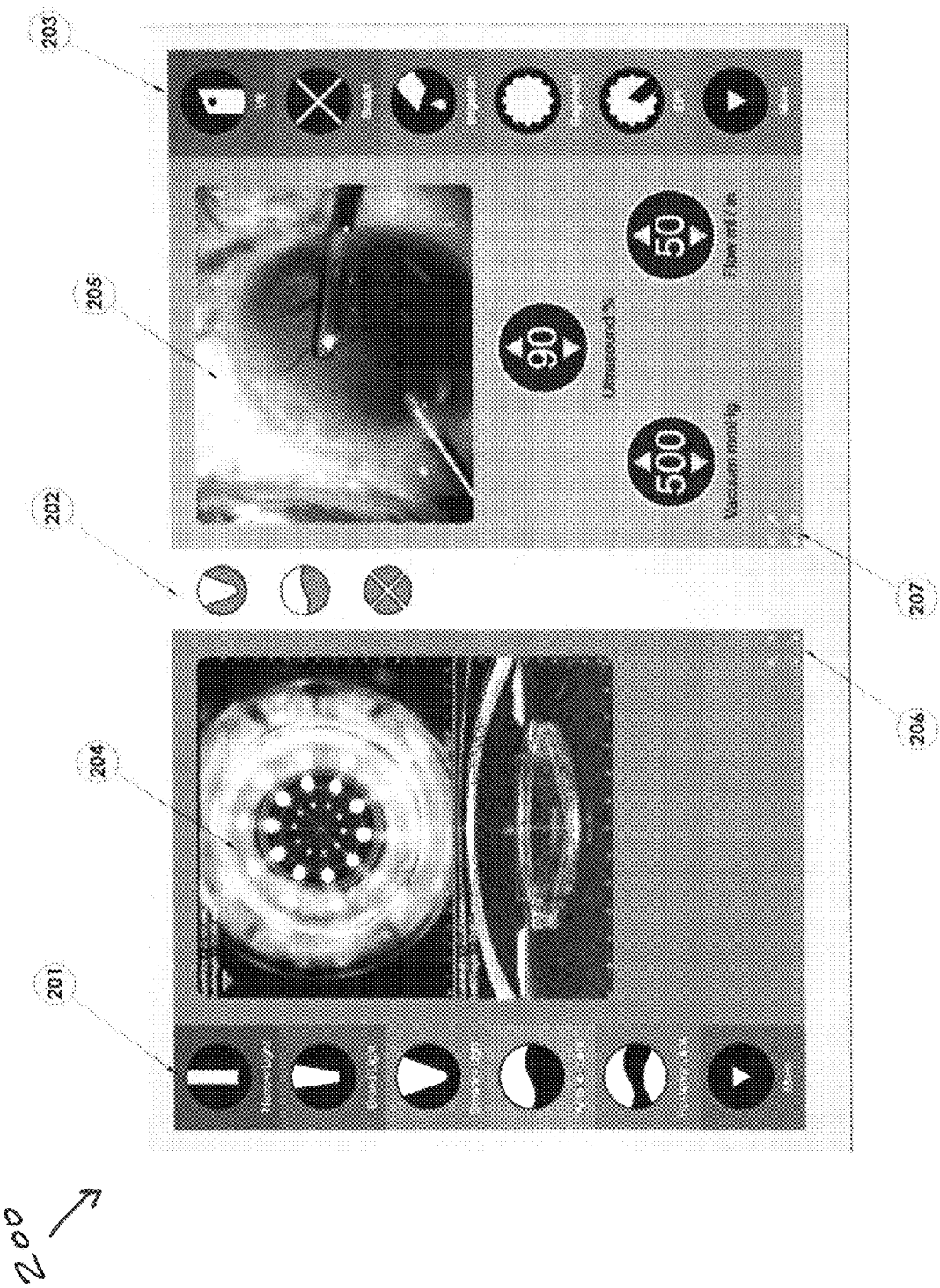
FIGS. 9-11 illustrate various views of one embodiment of a graphical user interface for a combination Femto-Phaco surgical device.
Figure 10:
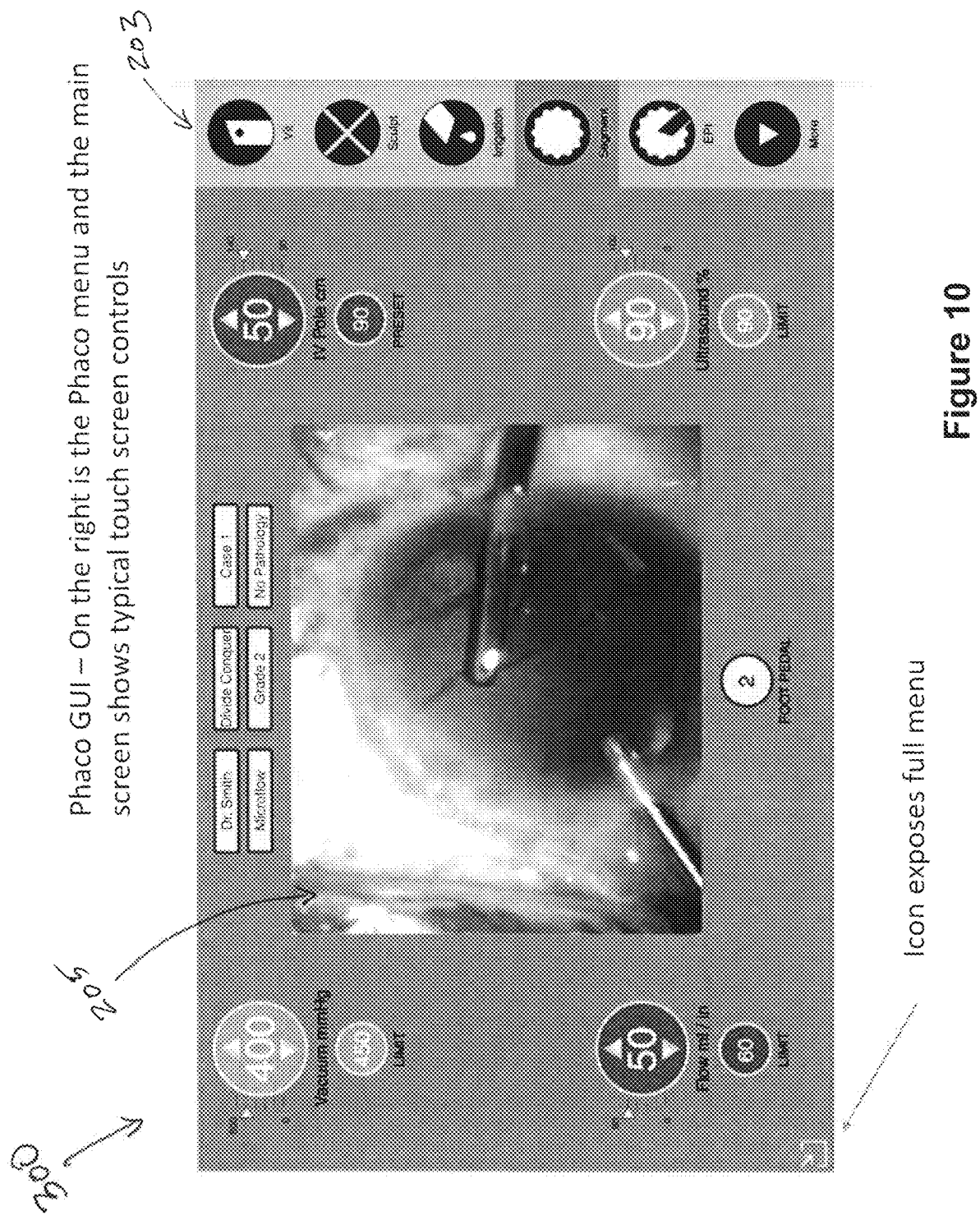
Figure 11:
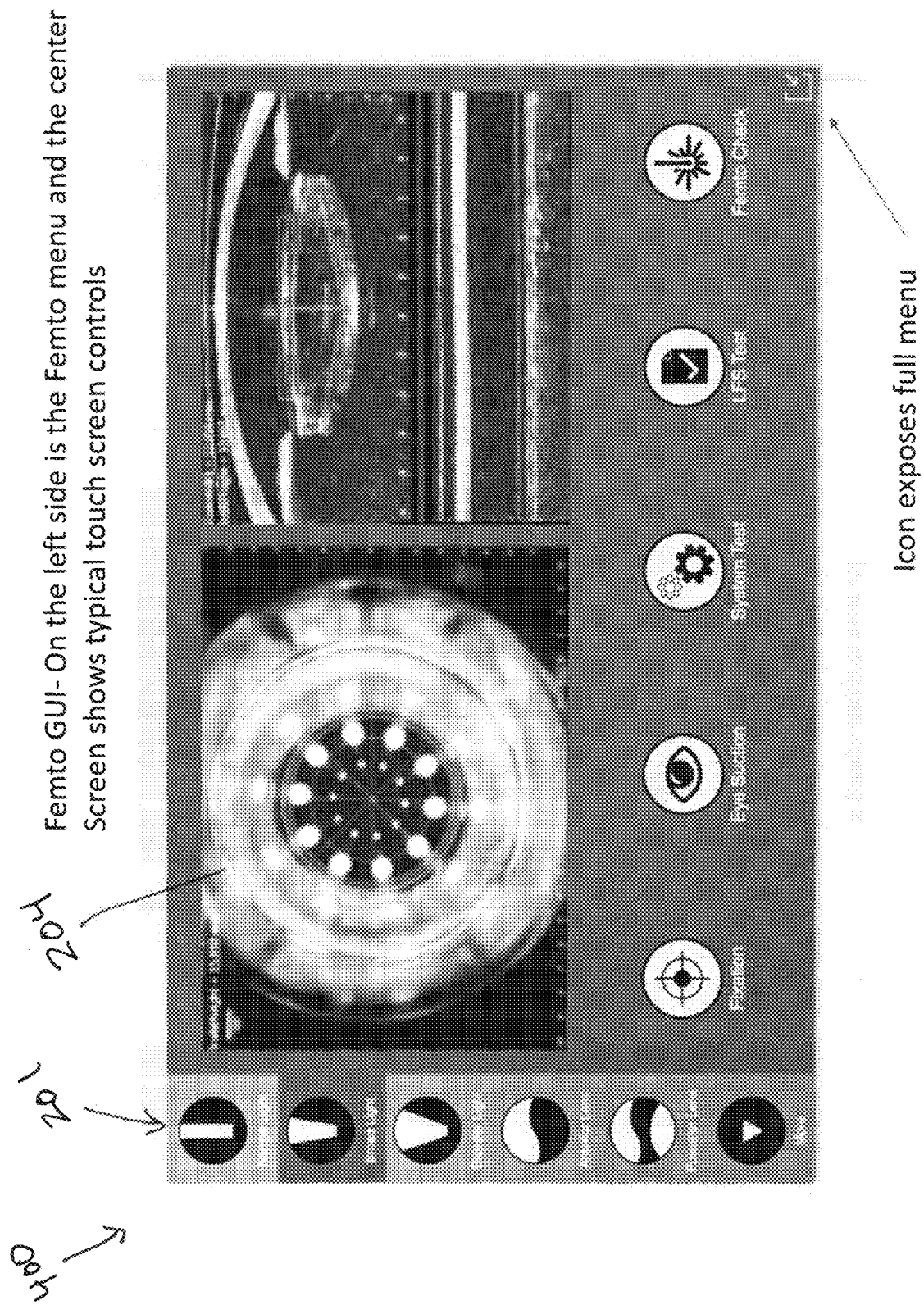

FIGS. 9-11 illustrates one embodiment of a user interface 200 for a combined Femto-Phaco surgical device, such as shown in FIGS. 1-8. As shown in FIG. 9, the interface 200 preferably includes a combined interface for use with both Femto and Phaco procedures.

The interface 200 advantageously includes a combined procedural Femto/Phaco icon control zone 202, which is a common procedural step central menu. The control zone 202 allows a surgeon or other professional to access procedural history from both Femto and Phaco procedures, and permits preset configurations and setting to be saved. The user interface 200 also permit the combination of information gained from the procedures, which could be used to predict the configuration for the next procedure for that patient or a future patient.

The interface 200 can also include a Femto vertical icon control zone 201 that is adjacent to a still image or live video 204 of a patient's eye. It is especially preferred that the various options/tools are presented in the order of their use in the Femto procedure.

Advantageously, interface 200 includes a Phaco vertical icon control zone 203, which is disposed adjacent to a Phaco microscope view of eye 205. In this manner, a surgeon or other professional can view controls and different view of a patient's eye simultaneously and on the same console/interface 200, which to Applicant's knowledge could not previously be done. The control zone 203 also preferably presents its icons in the order of their use during the Phaco procedure.

The interface 200 can further include icons 206 and 207 that permit one of the Femto or Phaco modes to be presented in full screen and thereby hide the other mode. In this manner, a surgeon or other professional can quickly and easily switch back and forth between a Femto mode, a Phaco mode, and a combined Femto-Phaco mode depending on what information and view is desired.

For example, FIG. 10 illustrates an exemplary interface 300 showing a full view screen of the Phaco portion of the interface 200 and includes the Phaco vertical icon control zone 203 and view of eye 205. The interface 300 may also include additional controls, and an icon to permit return to the combined interface 200.

In contrast, FIG. 11 illustrates an exemplary interface 400 showing a full view screen of the Femto portion of the interface 200 and includes the Phaco vertical icon control zone 203 and the still image or live video 204 of a patient's eye. The interface 400 may also include additional controls, and an icon to permit return to the combined interface 200.

Interface 200 is preferably presented on monitor 1 shown in FIGS. 1-8, and thereby can be easily viewed and accessed before, during, and after the procedures. As discussed above, the monitor 1 is coupled to the device 100 via a monitor arm 2, monitor tilt 3 and swivel 4, such that a viewing angle of the monitor 1 can be adjusted as needed.

Advantageously, the combined Phaco/Femto interface 200 presents both Femto and Phaco controls with the addition of a middle combined menu that illustrates integration systems and permits viewing of procedural history and saved presets for both platforms. This combined interface 200 permits a surgeon or other professional to quickly move back and forth between procedures. When combined with device 100, the surgeon or other professional can quickly and easily move from a Femto procedure to a Phaco procedure and vice versa with ease, and most importantly without moving the patient. This is critical especially where a cataract procedure may require only a minimum amount of one of Femto and Phaco procedures and a majority of the other, or where an ophthalmologist prefers to interrupt a Femto procedure and conduct a Phaco procedure and then return to the Femto procedure. With the prior art devices known to Applicant, this would require a complex arrangement and potential movement of the patient back and forth between the procedures. Using the device 100 described herein, an ophthalmologist could quickly move back and forth between procedures to obtain the optimal results, while reducing overall time required for the procedure.

Figure 16:
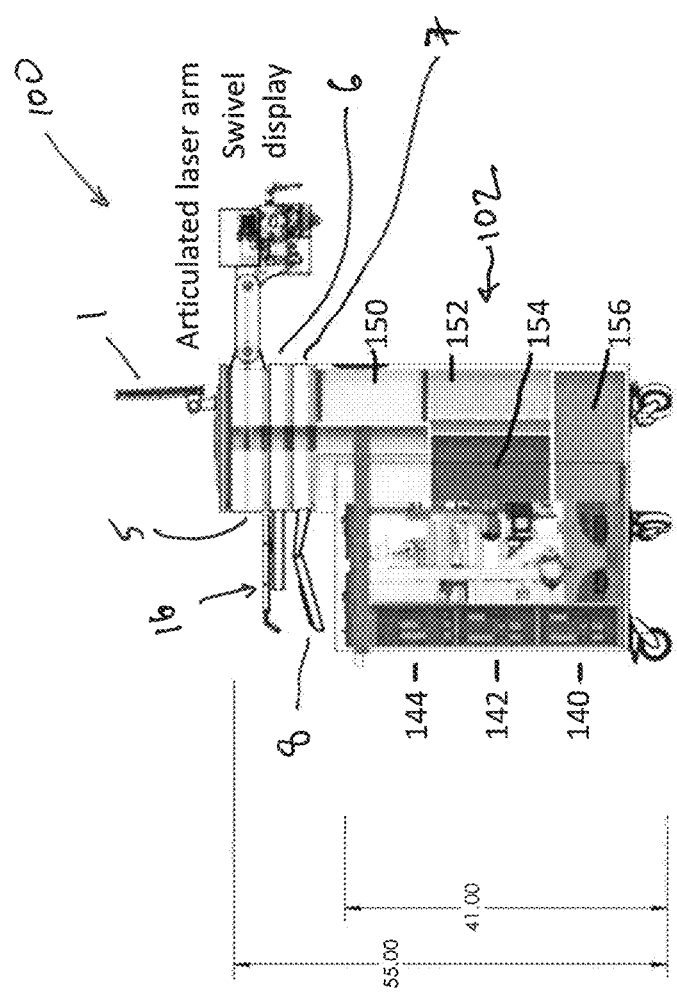
FIG. 16 illustrates a wireframe view of the components disposed within the housing of the combination surgical device of FIG. 1.

FIG. 16 illustrates the various components that may be disposed within the device 100 shown in FIG. 1. For example, device 100 can include a main computer (CPU) 140, circuitry 142 for the laser for the Femto procedure, a laser optical plate 144 for the Femto procedure, a fluidics module 150, a compressor 152, Phaco controller 154, and a power supply 156.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A combination Femto laser (Femto) surgical device and Phacoemulsification (Phaco) ophthalmic surgical device, comprising:
    a housing, the housing comprising a Femto surgical device and a Phaco surgical device;
    the housing having a plurality of articulating segments, wherein each of the segments is rotatable with respect to the housing;
    wherein a first segment of the plurality of articulating segments is coupled to the Femto surgical device via an articulating arm, wherein the Femto device comprising a Femto laser head and one or more accelerometers configured to provide x, y, and z position data of the Femto laser head;
    a memory device communicatively coupled to the one or more accelerometers and configured to record a use position of the Femto head as x, y, and z coordinates in three dimensional space and to transmit the use position following use of the Phaco surgical device;
    wherein a second segment of the plurality of articulating segments is coupled to a tray configured to hold a set of hand pieces for use in phacoemulsification;
    wherein a third segment of the plurality of articulating segments is coupled with a keyboard or keyboard tray;
    a display disposed on a top portion of the housing; and
    wherein the first segment and the second segment are independently rotatable about the housing.

2. The device of claim 1, wherein the Femto surgical device and the Phaco surgical system interface with a controller for controlling the Femto surgical device and Phaco surgical system.

3. The device of claim 1, wherein the controller permits a user to utilize both the Femto surgical device and Phaco surgical system without moving a patient.

4. The device of claim 1, wherein the Femto device and tray can move and articulate with respect to one other, such that movement of a patient is not required between the Femto and Phaco procedures.

5. The device of claim 1, wherein the Femto laser head is configured to move in a vertical X movement and horizontal Y movement or any angle to place the Femto laser head at a patient's eye or be removed from the patient's eye during surgery.

6. The device of claim 5, wherein the keyboard or keyboard tray is configured to move in a vertical X movement and horizontal Y movement or any angle with or independently from the Femto laser head.

7. The device of claim 1, wherein the tray is configured to hold a Phaco hand piece, a vitrectomy (VIT) hand piece, an irrigation hand piece and an aspiration hand piece.

8. The device of claim 1, wherein the tray is configured to articulate along X and Y axes or at any angle, such that the tray can be placed into the surgical field at or about a patient's eye height for a Phaco surgical procedure without requiring movement of the patient.

9. The device of claim 1, further comprising a microscope integrated into the housing that is movable along x and y axes or at any angle such that the microscope can move in or out of position for a Phaco procedure.

10. The device of claim 9, wherein the microscope is coupled with the housing via a fourth articulating segment that permits rotational movement of the segment and microscope about the housing.

11. The device of claim 1, wherein the housing comprises first and second portions, and wherein the Femto device or tray is stored about the first portion when not in use.

12. The device of claim 1, wherein the Femto device and tray are each configured to articulate from a central column of the housing to permit articulation from a central point and allow the Femto device and tray to be placed into surgical position before, during and after surgery without requiring movement of a patient.

13. The device of claim 12, wherein articulation from the central point is circular in the horizontal.

14. The device of claim 1, wherein the Femto device and tray is extendable and retractable relative to the housing in a vertical movement and can extend or retract and at any angle.

15. The device of claim 1, wherein the housing comprises a cylindrical shape having a central axis, and wherein each of the plurality of articulating segments are configured to articulate or rotate about the central axis.

16. The device of claim 15, wherein the first segment has a first diameter and the second segment has a second diameter equal to the first diameter.

17. The device of claim 15, wherein each of the plurality of articulating segments have a cylindrical shape.

18. The device of claim 1, wherein the device is configured so that the Femto head can be returned to the x, y, and z coordinates after the use of the Phaco surgical device.

19. A combination Femto laser (Femto) surgical device and Phacoemulsification (Phaco) ophthalmic surgical device, comprising:
    a housing defining a vertical axis and connected to a plurality of articulating segments, wherein each of the segments is rotatable around the vertical axis;
    wherein the housing comprises the Femto surgical device, a Phaco surgical device, interfaces and a controller for controlling both the femto laser surgery device and the phacoemulsification device;
    wherein a first segment of the plurality of articulating segments is coupled to the Femto surgery device via an articulating arm; wherein a second segment of the plurality of articulating segments is coupled to a tray configured to hold a set of hand pieces for use with the phacoemulsification device;

wherein a third segment of the plurality of articulating segments is coupled with a keyboard or keyboard tray;

a display disposed on a portion of the housing; and, wherein the first segment and the second segment are independently rotatable about the vertical axis of the housing;

wherein each of the first and the second segments are rotatable around the vertical axis between a first position away from the patient and a second position adjacent to the patient;

whereby the device can be configured without repositioning the housing with respect to a patient, to perform a laser procedure or phacoemulsification procedure.

\* \* \* \* \*